(12) United States Patent
Reynolds

(10) Patent No.: US 6,409,991 B1
(45) Date of Patent: Jun. 25, 2002

(54) TREATMENT AND SYSTEM FOR NICOTINE WITHDRAWAL

(76) Inventor: Mark Reynolds, 4 Sidehill Rd., Westport, CT (US) 06880

( * ) Notice: Subject to any disclaimer, the term of this patent is extended or adjusted under 35 U.S.C. 154(b) by 0 days.

(21) Appl. No.: 09/464,549

(22) Filed: Dec. 15, 1999

(51) Int. Cl.[7] .......................... A61K 9/68; A61K 31/465
(52) U.S. Cl. .......................... 424/48; 424/440; 426/3; 514/343
(58) Field of Search .............................. 514/343; D20/7; D6/514, 515, 517; 424/48, 440

(56) References Cited

U.S. PATENT DOCUMENTS

| | | | | |
|---|---|---|---|---|
| 3,845,217 A | * | 10/1974 | Ferno et al. | 426/3 NCG |
| 3,877,468 A | * | 4/1975 | Lichtneckert et al. | 131/2 NCG |
| 3,901,248 A | * | 8/1975 | Lichtneckert et al. | 131/2 NCG |
| 3,914,434 A | * | 10/1975 | Bohni | 424/343 |
| 4,284,650 A | * | 8/1981 | Goupic | 426/5 |
| 5,017,400 A | * | 5/1991 | Olinger et al. | 426/660 |
| 5,055,478 A | * | 10/1991 | Cooper et al. | 514/343 |
| 5,362,496 A | * | 11/1994 | Baker, I et al. | 424/435 X |
| 5,385,749 A | * | 1/1995 | Serpezloni et al. | 426/658 |
| 5,470,566 A | * | 11/1995 | Lutzen | 424/54 |
| 5,488,962 A | * | 2/1996 | Perfetti | 131/270 NCG |
| 5,512,306 A | * | 4/1996 | Carlsson et al. | 426/3 |
| 5,536,511 A | * | 7/1996 | Yatka | 426/5 |
| 5,549,906 A | * | 8/1996 | Santus, I | 424/440 X |
| 5,593,684 A | * | 1/1997 | Baker, II et al. | 424/435 X |
| 5,662,920 A | * | 9/1997 | Santus, II | 514/343 X |
| 5,721,257 A | * | 2/1998 | Baker, III et al. | 514/343 X |
| 5,900,230 A | * | 5/1999 | Cutler | 424/49 |
| 5,958,471 A | * | 9/1999 | Schwarz et al. | 426/3 |
| 6,054,119 A | * | 4/2000 | Hurme et al. | 424/52 |
| D430,436 S | * | 9/2000 | Shimbo et al. | D6/515 |

FOREIGN PATENT DOCUMENTS

EP            472428       *  2/1992

* cited by examiner

Primary Examiner—Shep K. Rose
(74) Attorney, Agent, or Firm—Handal & Morofsky

(57) ABSTRACT

A kit and associated method in which symptoms of nicotine withdrawal syndrome are relieved as well as addressing the associated weight gain issues and craving for sweets by combining nicotine replacement therapy with complementary dosages of xylitol.

2 Claims, 4 Drawing Sheets

TREATMENT AND SYSTEM FOR NICOTINE WITHDRAWAL

TECHNICAL FIELD

The present invention relates to a method for relieving nicotine addiction and in particular to a kit and associated method in which symptoms of nicotine withdrawal syndrome are relieved while addressing the associated oral cravings for sweets.

BACKGROUND

Cigarette smoking continues to be the major preventable cause of death in the United States resulting in nearly 400,000 deaths per year due to cancer and cardiovascular disease. Despite the potential adverse health effects, the vast majority of cigarette smokers are unable to cease smoking. The lack of smoking cessation success is thought to be related to the tobacco withdrawal syndrome or tobacco abstinence syndrome that most smokers experience during their attempts to quit.

As many as one third of heavy smokers who are now 35 years old will die before age 85 of diseases caused by their smoking. The estimated cost of health problems associated with smoking, including medical care, absenteeism, decreased work productivity, and accidents is estimated to be $56 billion per year.

Cigarette smoking has many adverse consequences. In addition to being one of the major preventable causes of death in the United States from lung cancer and coronary artery disease, smoking has been implicated in cancers of the larynx, pancreas, bladder, kidney, and cervix. Smoking during pregnancy has been shown to increase the incidences of still births, neonatal deaths, premature delivery, low birth weight, and fetal death.

Smoking also has adverse impacts on breast feeding: it reduces milk production, decreases the milk's vitamin C content, and increases colicky pain and diarrhea in the breast-fed infant. Hospital admissions for bronchitis and pneumonia are twice as high for children whose parents smoke. These children also have increased risk of cancer later in life.

Given the consistent demonstration of dose-dependent relationships between smoking and disease, evidence of reductions in health risks following smoking cessation, and experimental studies documenting carcinogenic effects of tobacco smoke in animals, few scientists question the causal nature of the relationship between smoking and illness.

Despite this, approximately 26% of the adults in the United States continue to smoke. Very few effective strategies for smoking cessation have been developed, and up to 80% of smokers who initially stop smoking will relapse within six months to a year. The potential success of smoking cessation efforts is impeded, in part, by the fact that many of the advantages of continuing to smoke are immediate while the disadvantages of smoking are delayed and probabilistic.

The lack of smoking cessation success is attributed, in part, to nicotine addiction. One third to one half of occasional cigarette smokers graduate to maladaptive use and to physical dependence on nicotine. In fact, addiction to nicotine, as described in past U.S. Surgeon General's reports on smoking, is widespread, with over 50 million smokers in the United States alone. As a result of the effects of nicotine, most tobacco-dependent persons never achieve lasting abstinence, and half of all smokers die prematurely of tobacco-related disease.

Greater understanding of the adverse health effects of tobacco consumption has led to an increase in research on the nature of nicotine addiction and its treatment.

Nicotine is a water-soluble and lipid-soluble base. When delivered in alkaline cigar and pipe smoke, smokeless tobacco, and some European cigarettes, nicotine is readily absorbed across the mucosal membranes of the mouth and nose, which explains the rapid absorption associated with smokeless tobacco. Cigarette smoke is acidic and must be inhaled to be absorbed effectively in the pulmonary alveoli, where absorption is rapid.

From the lung, nicotine is absorbed into alveolar capillary blood and carried to the heart and then to the brain and other organs. All widely marketed cigarettes deliver sufficient nicotine to establish and sustain dependence readily. Cigarettes contain 6 to 11 mg of nicotine, of which the smoker typically absorbs 1 to 3 mg, irrespective of the nicotine-yield ratings provided by the tobacco company. The typical pack-per-day smoker absorbs 20 to 40 mg of nicotine each day, achieving plasma concentrations of 25 to 35 mg per milliliter by the afternoon. The plasma half-life of nicotine is approximately two hours.

The effects of nicotine that are associated with dependence include increased expression of brain nicotine receptors, changes in regional brain glucose metabolism, electroencephalograph changes, the release of catecholamines, tolerance, and physiologic dependence. These effects increase the compulsion to smoke by producing positive reinforcement (with the administration of nicotine) and withdrawal symptoms (with abstinence).

Withdrawal symptoms are intensified by abrupt abstinence from nicotine, beginning within a few hours, peaking within a few days, and typically lasting for four weeks, although there is considerable variability. Most people who quit smoking relapse within one week, when withdrawal symptoms are at or near their peak. Thereafter, the correlation between withdrawal symptoms and relapse is weak.

For those who are unable to give up smoking completely, various forms of nicotine-replacement therapy have been suggested. Of the pharmacological approaches to aiding nicotine use cessation, nicotine replacement, e.g., via transdermal nicotine patches or nicotine gum, is the most widely used.

Nicotine-containing chewing gum is available commercially and has provided a satisfactory substitute for tobacco-smoking for some people. Nicotine gum and other transdermal nicotine delivery systems decrease abstinence discomfort, especially anxiety, decreased memory, and irritability. Furthermore, they increase the craving for sweets.

As such, one immediate consequence of quitting smoking is weight gain. There is overwhelming evidence that smoking cessation leads to weight gain. Various studies have shown that people who quit smoking gain weight. It was reported that smokers weighed an average of 7.13 lb (range: 2.36–14.99 lb) more than nonsmokers. Smokers who quit in the longitudinal studies gain an average of 6.16 lb (range: 1.76–18.07 lb) following cessation. A popular, but erroneous, statistic is that only about one third of smokers will gain weight following cessation, while one third stay the same weight and one third lose weight. Unfortunately, recent studies have confirmed that the overwhelming majority of smokers gain weight following cessation.

Unfortunately, weight gain following smoking cessation appears to be a significant reason for continued smoking. At least one third of smokers report that they continue to smoke primarily for the weight-related benefits. It also appears that some individuals, particularly females, are likely to initiate smoking because of the weight reduction properties of cigarettes. Weight-related concerns also appear to be an important predictor of success in both worksite and pharmacologic intervention.

Although weight and weight-related concerns appear to be a major reason for continued smoking, it may be surprising to learn that there are few effective treatment methods for reducing this inevitable weight gain. Behavioral methods, which are effective in weight control in general, have not yet been developed to the extent where they can prevent, or even reduce, postcessation weight gain. In terms of pharmacological intervention.

The most effective pharmacological approach thus far has been nicotine substitution therapy, using nicotine gum, or other nicotine forms, to slowly wean individuals from their addiction to nicotine and craving for tobacco products containing same. The problem with nicotine substitution therapy is that it involves the administration of the psychoactive constituent of tobacco indicated as a contributor to the diseases for which smoking is a risk factor. Nicotine substitution, additionally, must be tapered leading to nicotine withdrawal. Along with the tobacco cravings, the patient will often have sugar cravings. Addressing these cravings leads to cavities which is an unwelcome side effect.

Therefore, a continuing need exists for pharmacological treatments that will facilitate smoking cessation, e.g., by blocking or relieving nicotine withdrawal syndrome, or at least reducing the symptoms of nicotine withdrawal while acting as a weight management agent to address the associated sugar cravings.

It is further desirable that the treatment address the associated sugar cravings and subsequent tooth decay.

SUMMARY OF INVENTION

It is an object of the invention to address the deficiencies of the prior art heretofore discussed.

It is a further object of the invention to provide a treatment to treat nicotine addiction which addresses the associated side effects of nicotine withdrawal, namely sugar cravings and cavities.

A kit and associated method which may be auxiliary or ancillary to other treatments are provided to alleviate the symptoms of nicotine withdrawal while addressing associated sugar cravings and resulting cavities. The kit comprises a therapeutically effective amount of nicotine, nicotine metabolites or pharmaceutically acceptable salts thereof in a pharmaceutically acceptable carrier and multiple pieces of gum comprising a therapeutically effective amount of xylitol. The method comprises administering a therapeutically effective amount of nicotine, nicotine metabolites or a pharmaceutically acceptable salts thereof in a pharmaceutically acceptable carrier and multiple pieces of gum comprising a therapeutically effective amount of xylitol to a human in need of such treatment, to reduce nicotine withdrawal, sugar cravings, and resulting tooth decay. In preferred embodiments, the kit comprises multiple pieces of nicotine gum and xylitol gum with instructions for the patient to wean himself off nicotine.

DETAILED DESCRIPTION OF THE DRAWINGS

Figure 1:
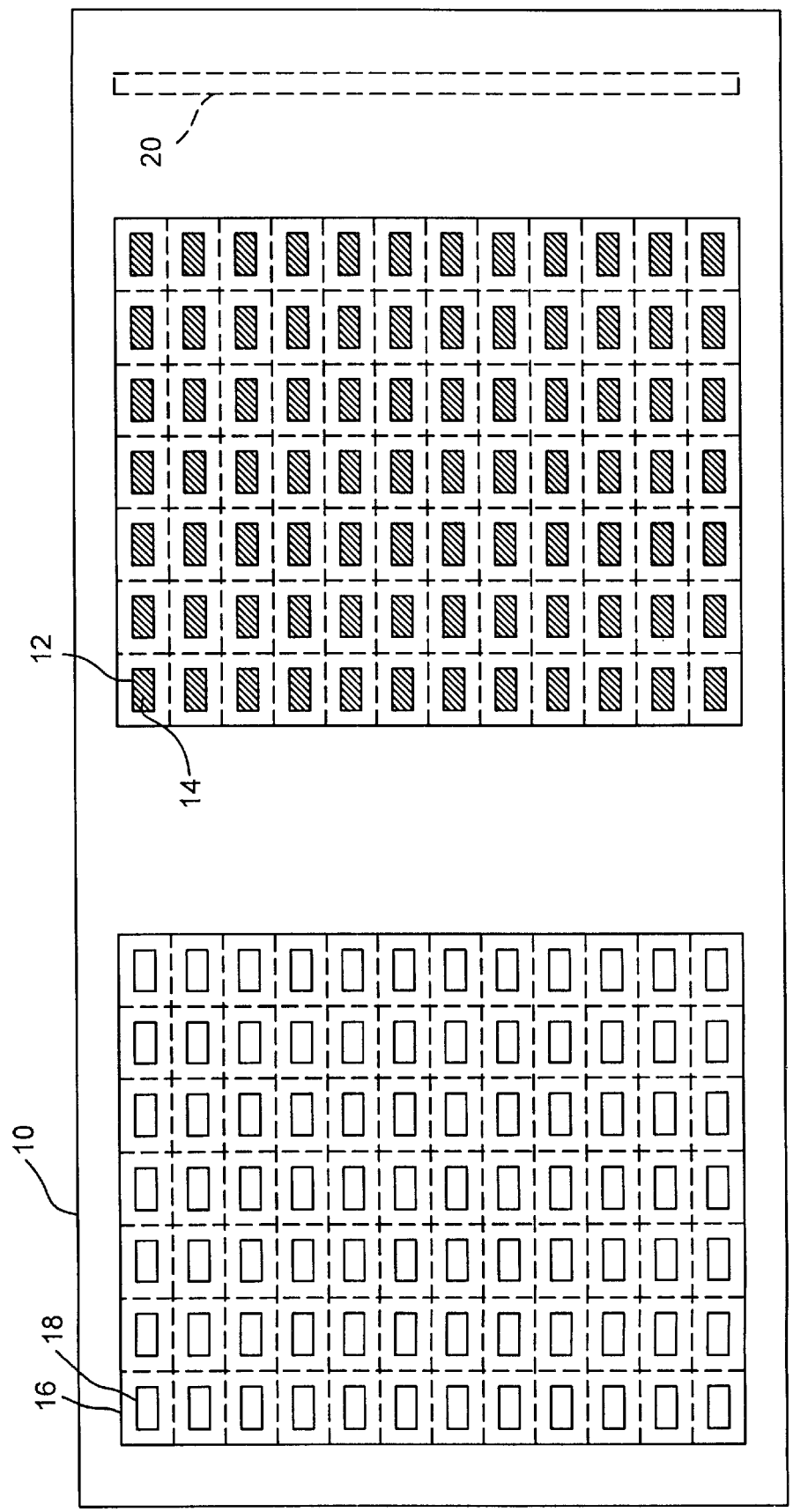
FIG. 1 shows a preferred embodiment of a phase one quitting smoking kit in accordance with the invention.

"Patient", as used herein, is generally meant to be a human. However, it is envisioned that the method of the present invention can be used to treat nicotine addiction in experimental mammals other than humans, such as primates other than humans, rats, mice, dogs, and the like. Using the methods of the present invention, mammals experimentally addicted to nicotine or both can be humanely weaned from the substance, and the physiological and psychological damage or changes which result from past nicotine use or abuse can be assessed. In addition, these mammals can be used to study the progression of or recovery from such physiological and psychological damage or changes subsequent to the patient's abandoning or reducing his, her, or its nicotine use. In the controlled environment of the laboratory, the non-human mammalian patient would be allowed to develop a nicotine addiction and to maintain this addiction for a prescribed period of time. The patient's addiction would then be treated in accordance with the method of the present invention to cause the patient's use of nicotine to decrease or cease. The patient could then be monitored over time from the time of nicotine use cessation or reduction to ascertain long-term physiological or psychological changes or damage and the patient's recovery from these changes or damage.

As used herein, "addicted to" and "addiction to" a substance (and other forms of this phrase) means a habitual or recurrent use of the substance. It is meant to include, but is not meant to be limited to, a dependency on the substance. Dependency is characterized by a patient's persistence in substance use or abuse or the recurrence of such use or abuse in the face of negative social or medical consequences of this use or abuse or in face of the patient's declared or undeclared intent to abandon or reduce his or her use of the substance. A patient's dependency can be manifested in objective criteria or other indices of nicotine seeking behavior, such as repeated attempts to abandon use or abuse of nicotine, as evidenced by, for example, past participation in encounter groups designed to reduce the participants' smoking (or use of other nicotine delivery systems) and hospitalization for complications arising from smoking (or use of other nicotine delivery systems), including chronic bronchitis, lung infection, lung cancer, oral cancer, throat cancer, coronary disease, emphysema, and the like. Addiction to nicotine can be manifested by the patients' inability to stop, for a substantial period of time, such as one year or more, the use of tobacco products, such as cigarettes, cigars, pipe tobacco, chewing tobacco, and the like.

The inventive kit and method to treat a patient addicted to nicotine by addressing one of the most common side effects of nicotine withdrawal by combining nicotine replacement therapy with an agent to reduce the sugar cravings and the resulting cavities from the added ingestion of sugar, that agent being xylitol.

Xylitol is a sugar alcohol. Xylitol is most often used in sugarless gums. One of the unique properties of xylitol is that it reduces caries in oral care preparations. Thus, it is recommended for use in gum. Dentists recommend that patients chew sugarless gum after meals to prevent or reduce the chances for cavities.

The invention is unique in that it is a simple and cost effective method of treating nicotine withdrawal and its associated symptoms of sugar cravings and cavities. In preferred embodiments, the invention is presented in kits comprising multiple pieces of nicotine gum and multiple pieces of xylitol gum. Nicotine gum is commercially sold under the trademark NICORETTE and is sold in kits containing gum in either a 4 mg strength or 2 mg strength. Nicotine gum is a form of nicotine replacement therapy. The chewing pieces provide nicotine to the patient's system to work as a temporary aid to help the patient quit smoking by reducing nicotine withdrawal symptoms. Nicotine gum achieves results by functioning as a transdermal delivery system to deliver nicotine. The patient does not chew nicotine like chewing gum. Rather the patient takes a few slow, deliberate bites (15 or so) until he gets a tingle and then parks it between the cheek and gum for about a half hour.

The manufacturers of NICORETTE recommend that those who smoke more than 24 cigarettes a day (heavy smokers) should use a 4 mg nicotine dosage every one to two hours.

The inventive xylitol gum contains at least enough xylitol to taste sweet, preferably at least 50% by weight. 670 mg of xylitol in a 1 gram piece of gum provides excellent taste characteristics.

A piece 14 of the inventive nicotine gum 12 used in accordance with the system of the present invention comprises 2 mg of nicotine in the form of nicotine extract or powdered tobacco, 670 mg of xylitol, 350 mg of gum base, and the customary small amounts of natural flavors, glycerine and lecithin, hereafter referred to as "nicotine" gum. In accordance with the invention, the kit also comprises a nicotine-free xylitol gum. The nicotine-free "xylitol" gum comprises 670 mg of xylitol, 350 mg of gum base, and the customary small amounts of natural flavors, glycerine and lecithin, hereafter referred to as xylitol gum. In accordance with the present invention, the xylitol gum is white. The nicotine gum is given a color to differentiate it from the xylitol gum. This color may be green, pink or other suitable color. In accordance with the invention, it is also contemplated that both the xylitol gum and the nicotine gum will be given the same flavor to easy transition from nicotine gum to all xylitol gum. Other flavors of gum will be introduced.

During phase one of the inventive procedure, which comprises the first six weeks of treatment, the patient wishing to quit smoking uses a plurality of phase one kits comprising a selection of gums, arranged in accordance with the preferred embodiment of the invention. FIG. 1 shows a preferred embodiment of a phase one kit 10. In accordance with the invention, the weekly dosage of nicotine in single phase one kit 10 is selected to be equal to the nicotine dosage objective at the end of phase one.

Accordingly, the phase one kit comprises seven sleeves 12 of nicotine gum 14, each sleeve having twelve pieces of gum. The phase one kit also comprises seven sleeves 16 of xylitol gum 20 which the patient is instructed to use instead of the nicotine gum 14 when the urge to smoke strikes between dosages of the nicotine gum. In accordance with the invention it is contemplated that the gum will be taken by the patient two at a time every two hours at the end of phase one.

For the first six weeks an average to heavy smoking patient takes two pieces of nicotine gum 14 every 1 to 2 hours. Instructions 20 direct the smoker to use the nicotine gum 14 only when nicotine cravings are felt and to try to delay use of the gum 14 as long as possible after the cravings in order to hasten recovery. Gum containing xylitol, but not nicotine, may be used by the user as a means for alleviating cravings, thus enabling the person quitting smoking to put off use of nicotine gum. The patient is also instructed to try to use two pieces of gum 14 every two hours. This will correspond to a single daily sleeve everyday, giving the patient an easy gauge against which to measure his progress.

When the patient is using only one sleeve 12 of the phase one kit 10 each day, for a period of one week, he is prepared to enter phase two of the treatment. Patients are also urged to maintain levels on non-use of nicotine. In other words, once a particular low level of nicotine consumption is achieved over a period of time, for example, a week, the patient is urged never to increase the level from week to week.

When there are cravings for nicotine, in between nicotine gum dosages, the patient is directed to use the xylitol gum 18. For times when the cravings are particularly difficult, the patient may take an extra piece of nicotine gum 14 and a piece of xylitol gum 18. Additionally, as most patients experience oral cravings, such as a craving for sweets, when there is a craving, another piece of xylitol gum 18 may be taken.

Figure 2:
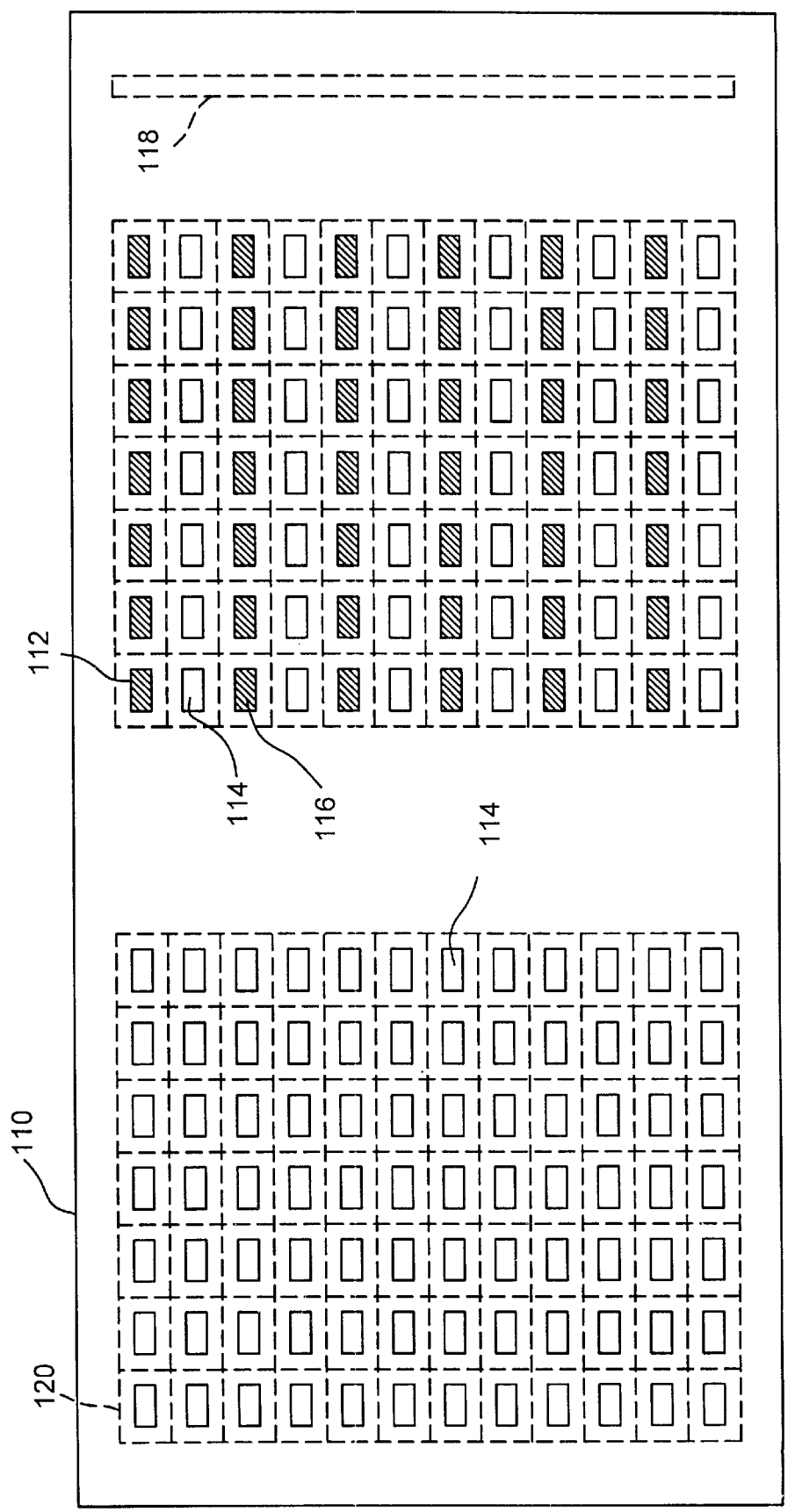
FIG. 2 shows a preferred embodiment of a phase two quitting smoking kit in accordance with the invention.

FIG. 2 shows a preferred embodiment of the phase two kit 110 which comprises seven sleeves 112 of gum, each sleeve having six pieces of white xylitol gum 114 and six pieces of tinted nicotine gum 116. In weeks 7 through 9, instructions 118 direct the patient to use a phase two kit 110 each week, taking one piece of nicotine gum 116 together with one piece of xylitol gum 114 every 1 to 2 hours. The phase two kit 110 preferably also includes additional xylitol gum sleeves 120 to address cravings between dosages.

Figure 3:
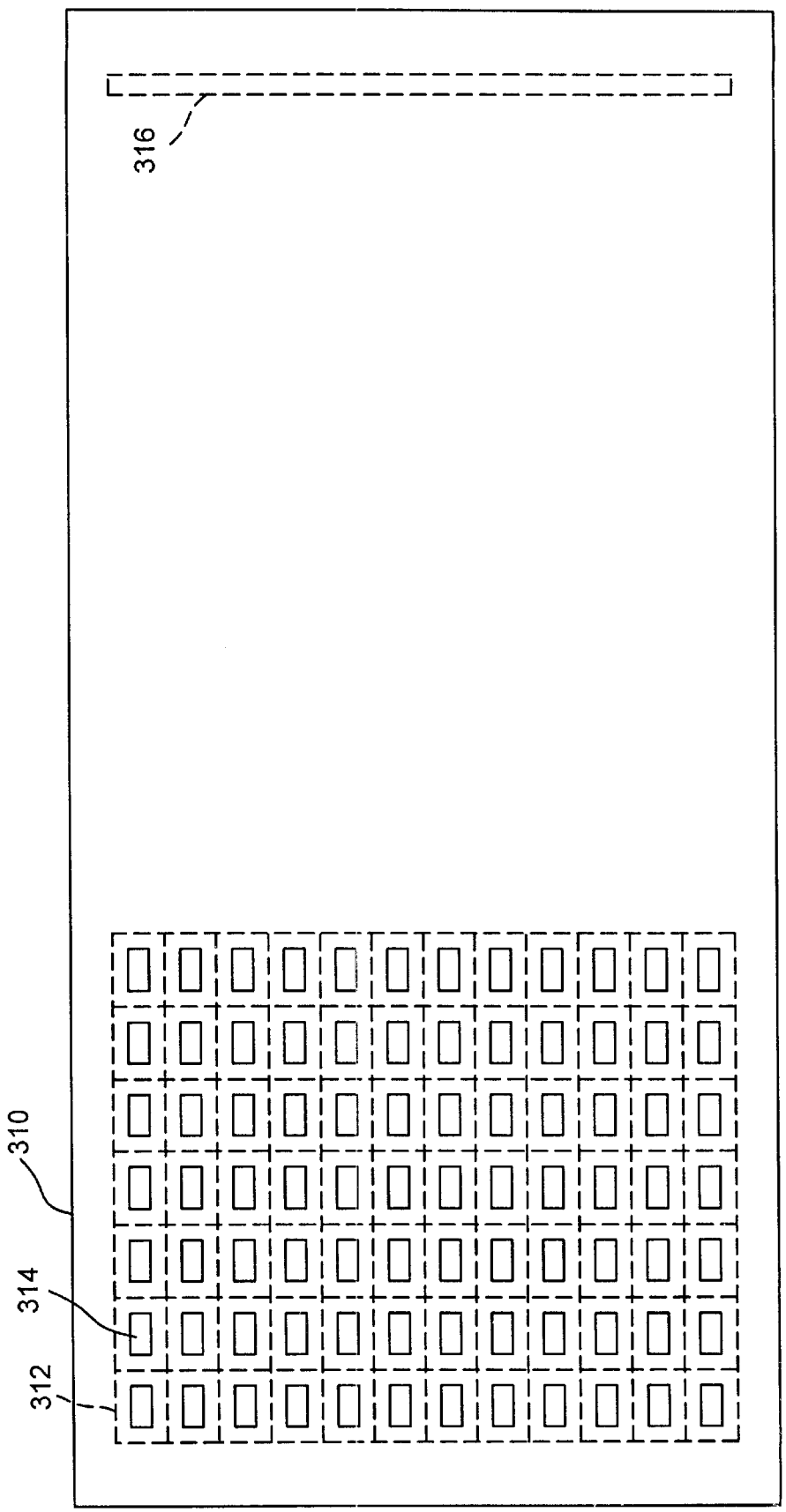
FIG. 3 shows a preferred embodiment of a phase three quitting smoking kit in accordance with the invention.

FIG. 3 shows a preferred embodiment of a phase three kit 310. In weeks 10 through 12, the patient uses one phase three kit 310 each week. The phase three kits 310 each have seven sleeves 312 of xylitol gum 314, twelve pieces in each sleeve. During this period the patient is counseled by instructions 316 to reduce the consumption of the gum 314 generally, and to limit its use to after meals and after snacks, thus using the xylitol gum 314 to minimize dental cavities. After twelve weeks, the patient chews xylitol gum 314 every four to eight hours or as needed.

In accordance with an alternative embodiment of the invention, the sleeve of gum which contains all nicotine gum in phase one is given one color, the sleeve of gum in phase two which contains nicotine gum and xylitol gum has both these gum is tinted in two other colors, and one of the sleeves of gum in the phase three kit is tinted a fourth color. In all of the kits, a sleeve of white xylitol gum is included. The objective here is to psychologically condition the patient to the fact that the colored gums are a medication designed to relieve the addiction to cigarettes. This is completely true in the case of the phase one kit but varies until the phase three kit is being used, and this kit has tinted gum which has no nicotine, but psychologically the tinting enables the patient to better accept the complete withdrawal of nicotine from his body.

The program helps wean the patient from nicotine, by gradually decreasing the dosage until the patient stops using the nicotine gum altogether and starts to use the xylitol gum instead, particularly after eating sweets. The xylitol chewing gum has no known side effects and addresses the patient's need for oral satisfaction and oral satisfaction. Furthermore, the xylitol gum is non-carcinogenic and has in numerous studies clinical studies been demonstrated to reduce the incidence of caries in the population.

An alternate embodiment of the invention includes a third set of gum in a different color, said gum comprising lobeline or a mixture of lobeline and oat seed (or metabolites thereof). Lobeline has a chemical structure and physiological effects that are similar to nicotine and is believed to mask the withdrawal symptoms of nicotine addiction without itself being addictive. The recommended daily dosage of lobeline is 20 to 40 drops of a 10% solution of lobeline 3 to 5 times per day.

In accordance with the above example, in the phase one kit, instead of twelve pieces of tinted nicotine gum in a sleeve, there would be would be eight pieces of nicotine gum and four pieces of lobeline gum so that the patient would have a lobeline gum every third dose. In the phase two kit, instead of six pieces of tinted nicotine gum in a sleeve, there would be would be three pieces of nicotine gum and three pieces of lobeline gum so that the patient would have a lobeline gum every other dose. In the phase three kit, there would be extra pieces of lobeline gum to address severe nicotine cravings.

Because the use of large and frequent doses of lobelia may induce nausea or vomiting in some sensitive individuals, the above dosages may have to be decreased. For such individuals, the kits may further contain gum comprising St. John's Wort to address nervous withdrawal symptoms. The recommended daily dosage of St. John's Wort is 20 to 40 drops of a 20% solution of lobeline in 3 to 5 times per day. Alternatively, instead of separate gum, the lobeline gum may also contain St. John's Wort.

In one preferred embodiment of the invention, both the nicotine and the xylitol are delivered in gum form as discussed above. However, a unique advantage of the invention is that the nicotine is not limited to being delivered in gum form as the xylitol gum addresses the need for oral satisfaction. So it is now possible to administer nicotine, nicotine metabolites and/or their pharmaceutically acceptable salts thereof as the pure chemicals. Optionally, other therapeutic and/or prophylactic ingredients may be added. The carrier(s) must be acceptable, in the sense of being compatible with the other ingredients of the formulation and not deleterious to the recipient thereof.

Figure 5:
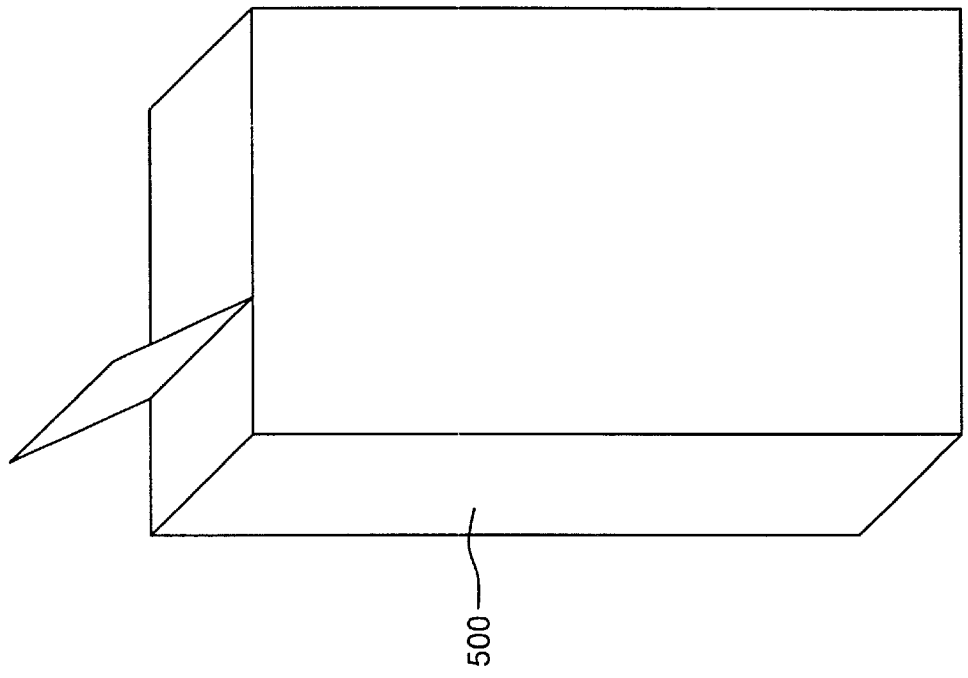
FIG. 5 shows a second preferred embodiment for packaging the present invention.
Figure 4:
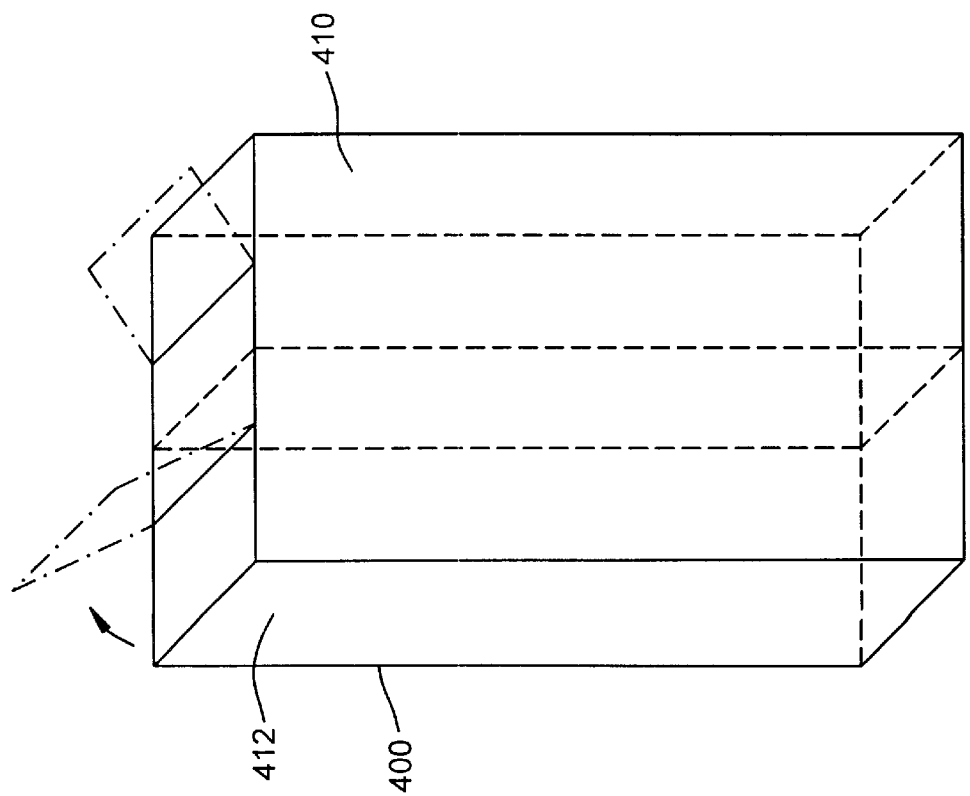
FIG. 4 shows a preferred embodiment of packaging of the present invention.

As doses of the nicotine and/or xylitol gum will have to be taken throughout the day, it is desirable to have provide the gum in packaging which is aesthetically acceptable as well as discrete in appearance. Referring to FIG. 4, a two compartment package 400 is provided. The first compartment 410 contains nicotine gum, while the second compartment 412 contains xylitol gum. The gum is preferably color coded so that the user may distinguish the nicotine gum from the xylitol gum. In preferred embodiments, each compartment has its own lid which allows access to only one side of the package at a time. Preferably, the package does not have any markings to indicate that nicotine gum is contained therein so the user will be able to control their nicotine cravings in a discrete manner. Additionally, the packaging is ideal for storing the Stage 1 system and can be adapted for the stage 2 and 3 systems. However, for the stage 2 and 3 systems where there are additional doses of xylitol gum, the package 500 shown in FIG. 5 may be used where the package contains only one type of gum. In preferred embodiments, the package is the size a standard cigarette package so that it may be fit into the user's old cigarette carrying case so that the user does not have to give up the use of the accessory but rather uses the accessory to enhance the program.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal and sublingual) administration. The formulations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the active ingredient from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, prefilled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, a nicotine metabolite or combination of nicotine metabolites may be formulated as ointments, creams or lotions, or as the active ingredient of a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

In accordance with the method of the present invention, delivery of topical nicotine is combined with the provision of xylitol chewing gum, as detailed above for the purpose of satisfying cravings, oral stimulation and prevention of cavities in the teeth by killing in the streptococcus which causes tooth decay.

Formulations suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier. When desired, the above-described formulations can be adapted to give sustained release of the active ingredient employed, e.g., by combination with certain hydrophilic polymer matrices, e.g., comprising natural gels, synthetic polymer gels or mixtures thereof.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

The pharmaceutical compositions according to the invention may also contain other adjuvants such as flavorings, colorings, antimicrobial agents, or preservatives.

It will be further appreciated that the amount of a nicotine metabolite or combination of nicotine metabolites, or their active salts or derivative thereof, required for use in treatment will vary not only with the particular salt selected but also with the route of administration, the nature of the condition being treated and the age and condition of the patient and will be ultimately at the discretion of the attending physician or clinician.

In general, however, a suitable dose will be in the range of from about 1 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day, calculated as the nicotine metabolite in the free base form.

Also in accordance with the present invention, a preferred gum may be made by reducing the amount of nicotine to half that described alone in connection with the figures and instructing the person quitting smoking to take twice as many nicotine containing gum tablets so that the nicotine dosage is the same.

In accordance with the present invention, it is contemplated that the xylitol and nicotine dosages outlined above for chewing gum pieces may be delivered using another vehicle, such as a packet of the xylitol laced with the above described dosages of nicotine. In addition, the nicotine free gum with xylitol and no nicotine may also be replaced by a packet of the xylitol. Such packets, containing xylitol and nicotine in one instance, and xylitol only in the other instance, may include additional inert materials to increase their volume, as required, or may simply be pure. Generally, in accordance with the invention, such packets may be substituted for the analogous gum pieces described above, and used with the same frequency and strength described above. It is anticipated in accordance with the present invention that dosages of xylitol and nicotine may be taken by the patient by direct ingestion of the contents of a packet.

It is also contemplated in accordance with the invention that the packet of the xylitol and nicotine, as well as the packets of xylitol without nicotine to be used as a means for controlling tooth decay and dealing with oral urges, may be used as xylitol sweetener, the packet being opened and emptied into coffee, tea, milk, chocolate milk, lemonade or other suitable carrier.

While some illustrative embodiments of the invention have been described above, it is, of course, understood that various modifications will be apparent to those of ordinary skill in the art. Such modifications are within the spirit and scope of the invention, which is limited and defined only by the appended claims.

What is claimed is:

1. A therapeutic method to alleviate the craving associated with cessation of nicotine use in a human comprising: administering to a human in need of such treatment a combination of a first treatment and a second treatment, the first treatment comprising a therapeutically effective amount of nicotine, a nicotine metabolite or combination of nicotine metabolites or their pharmaceutically acceptable salts thereof to alleviate nicotine cravings and the second treatment comprising a therapeutically effective amount of xylitol to help reduce dental caries and alleviate oral cravings, wherein said first treatment comprises a plurality of pieces of substantially zylitol-free nicotine gum, each of said pieces of nicotine gum containing 2–4 mg of nicotine and said second treatment comprises multiple pieces of substantially nicotine-free xylitol gum each of said pieces of xylitol gum comprising at least 1 mg of xylitol.

2. A therapeutic method to alleviate the craving associated with cessation of nicotine use in a human comprising: administering to a human in need of such treatment a combination of a first treatment and a second treatment, the first treatment comprising a therapeutically effective amount of nicotine, a nicotine metabolite or combination of nicotine metabolites or their pharmaceutically acceptable salts thereof to alleviate nicotine cravings and the second treatment comprising a therapeutically effective amount of xylitol to help reduce dental caries and alleviate oral cravings, wherein said first treatment comprises a plurality of pieces of substantially xylitol-free nicotine gum, each of said pieces of nicotine gum containing 2–4 mg of nicotine and said second treatment comprises multiple pieces of substantially nicotine-free xylitol gum each of said pieces of xylitol gum comprising at least 670 mg of xylitol.

* * * * *